(12) United States Patent
Ouchouche

(10) Patent No.: US 10,022,533 B2
(45) Date of Patent: Jul. 17, 2018

(54) REINFORCEMENT MEMBER FOR A MEDICAL LEAD

(71) Applicant: Medtronic Bakken Research Center B.V., Maastricht (NL)

(72) Inventor: Sébastien Jody Ouchouche, Waalre (NL)

(73) Assignee: Medtronic Bakken Research Center B.V., Maastricht (NL)

(*) Notice: Subject to any disclaimer, the term of this patent is extended or adjusted under 35 U.S.C. 154(b) by 59 days.

(21) Appl. No.: 14/782,754

(22) PCT Filed: Mar. 27, 2014

(86) PCT No.: PCT/EP2014/056204
§ 371 (c)(1),
(2) Date: Oct. 6, 2015

(87) PCT Pub. No.: WO2014/166754
PCT Pub. Date: Oct. 16, 2014

(65) Prior Publication Data
US 2016/0038731 A1 Feb. 11, 2016

(30) Foreign Application Priority Data
Apr. 8, 2013 (EP) .................................. 13162805

(51) Int. Cl.
*A61N 1/00* (2006.01)
*A61N 1/05* (2006.01)
*A61B 17/00* (2006.01)

(52) U.S. Cl.
CPC ............. *A61N 1/0534* (2013.01); *A61N 1/05* (2013.01); *A61B 2017/00314* (2013.01)

(58) Field of Classification Search
CPC ............................................ A61B 2017/00314
See application file for complete search history.

(56) References Cited

U.S. PATENT DOCUMENTS 7,725,179 B2 5/2010 Maxfield et al.
7,833,191 B2 11/2010 Flach et al.
(Continued)

FOREIGN PATENT DOCUMENTS

| | | |
|---|---|---|
| EP | 1649889 A1 | 4/2006 |
| EP | 2110155 A1 | 10/2009 |
| WO | 2004110542 A2 | 12/2004 |

OTHER PUBLICATIONS

International Search Report and Written Opinion from International Application No. PCT/EP2014/056204, dated May 27, 2014, 11 pp.

*Primary Examiner* — Christopher D Koharski
*Assistant Examiner* — Elizabeth K So
(74) *Attorney, Agent, or Firm* — Shumaker & Sieffert, P.A.

(57) ABSTRACT

The present invention relates to a reinforcement means (400) for a lead (300), especially a lead (300) for neural applications, preferably a lead (300) for a neurostimulation and/or neurorecording system, wherein the reinforcements means (400) has at least predetermined and/or customizable bending motion capabilities and/or is configured such that the minimum bending radius of the lead (300) is at least partially limited. Furthermore, the present invention relates to a lead, a neurostimulation and/or neurorecording system and an interlocking annular element for a reinforcement means.

20 Claims, 3 Drawing Sheets

(56) References Cited

U.S. PATENT DOCUMENTS

Figure 1:
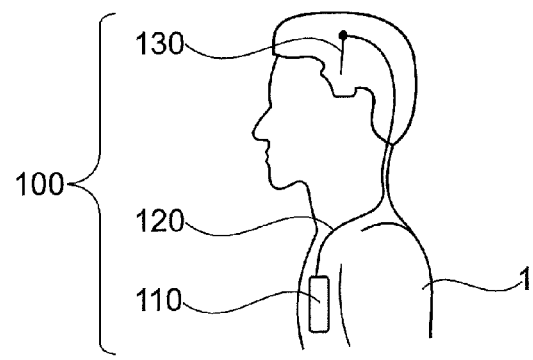

2012/0184836 A1 7/2012 Kolberg et al.
2013/0274843 A1* 10/2013 Barker .................. A61N 1/0534
607/116

* cited by examiner

REINFORCEMENT MEMBER FOR A MEDICAL LEAD

The present invention relates to a reinforcement means for a lead, especially for a lead for neural applications, a lead, a neurostimulation and/or neurorecording system and an interlocking annular element for a reinforcement means.

Implantable neurostimulation devices have been used for the past ten years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In existing systems, the probes are connected to an implantable current pulse generator.

Currently, systems are under development with more, smaller electrodes in a technology based on thin film manufacturing. These novel systems consist of a lead made from a thin film based on thin film technology, as e.g. described in WO 2010/055453 A1. The thin films are fixed on a carrier material to form a probe. These probes will have multiple electrode areas and will enhance the precision to address the appropriate target in the brain and relax the specification of positioning. Meanwhile, undesired side effects due to undesired stimulation of neighbouring areas can be minimized.

Leads that are based on thin film manufacturing are e.g. described by U.S. Pat. No. 7,941,202 and have been used in research products in animal studies.

In existing systems, the DBS lead has e.g. four 1.5 mm-wide cylindrical electrodes at the distal end spaced by 0.5 mm or 1.5 mm. The diameter of the lead is 1.27 mm and the metal used for the electrodes and the interconnect wires is an alloy of platinum and iridium. The coiled interconnect wires are insulated individually by fluoropolymer coating and protected in an 80 A urethane tubing. With such electrode design, the current distribution emanates uniformly around the circumference of the electrode, which leads to stimulation of all areas surrounding the electrode.

The lack of fine spatial control over field distributions implies that stimulation easily spreads into adjacent structures inducing adverse side-effects in about 30% of the patients. To overcome this problem, systems with high density electrode arrays are being developed, providing the ability to steer the stimulation field to the appropriate target.

Silicone-based electrode arrays have long been used as high density electrode arrays, such as the Michigan array or the Utah array. However, the mechanical mismatch between the stiff probe and soft biological tissue may cause inflammation at the implant site. The inflammation encourages the formation of glial scar which encapsulates the probe and thus isolates the electrodes.

Therefore, implantable devices with a soft and flexible base structure are needed. Polyimide is traditionally chosen as the mechanical supporting and electrical insulation material for many such implantable electrode designs due to its biocompatibility, lower stiffness and ease of fabrication. However, polyimide suffers from high moisture absorption, which can lead to metal delamination from the polymeric substrate.

To overcome this problem, microelectrode arrays which are mechanically supported and electrically insulated by other flexible materials such as Liquid Crystal Polymer (LCP) or Parylene are currently being developed. Various conductive materials like gold, platinum are used for the electrodes or traces connecting them and interconnecting processes such as ultrasonic bonding, ball bonding etc. are used to connect them to silicone-based shanks or PCBs with signal processing circuits.

One other alternative is to form an integrated thin film lead having a plurality of electrodes forming a complex electrode geometry, wherein the electronics of the lead are partially integrated into the lead and the thin film, the thin film e.g. providing both flexible microelectrode array and micro fabricated conductors. Once integrated in the flexible lead body of the lead, the electrodes and conductors must survive the implantation procedure as well as exhibit long term reliability.

It is therefore an object of the present invention, to improve a reinforcement means for a lead, especially for a lead for neural applications, a lead, a neurostimulation and/or neurorecording system and an interlocking annular element for a reinforcement means, in particular in that the electrodes and conductors of a lead according to the integrated thin film approach will survive the implantation procedure as well as exhibit long term reliability.

The above object is solved according to the present invention by a lead according to claim 1. Accordingly, a reinforcement means for a lead is provided, wherein the reinforcement means has at least predetermined and/or customizable bending motion capabilities and/or is configured such that the minimum bending radius of the lead is at least partially limited.

By this, the advantage is achieved that the electrodes and conductors of a lead according to the integrated thin film approach will survive the implantation procedure as well as exhibit long term reliability.

Additionally, a medical lead with predetermined bending motion capabilities to protect fragile conductors and electrodes from excessive mechanical stresses induced by the bending of the medical lead may be provided.

Since the reinforcement means has at least predetermined and/or customizable bending motion capabilities and/or is configured such that the minimum bending radius of the lead is at least partially limited the lead is not a completely stiff element and may allow the physician during implantation slight adjusting movements of the lead in order to correctly place and implant the lead, e.g. into the brain. But at the same time, the lead receives by means of the reinforcement means the necessary stiffness which is also needed for the implantation of the lead, in particular for the correct placement and the necessary accuracy thereof.

Furthermore, it is possible that the reinforcement means is configured such that the reinforcement means is at least partially arrangeable over and/or around and/or within and/or inside the lead and/or that the reinforcement means has at least partially a tubular shape or is at least partially forming a tube.

Moreover, it is possible that the reinforcement means comprises at least one slot, wherein the slot is configured and/or shaped to allow at least a partial bending of the reinforcement means.

By this design of the reinforcement means an easy and reliable solution can be provided to ensure that the lead being provided with at least one reinforcement means has predetermined and/or customizable bending motion capabilities and that the minimum bending radius of the lead is at least partially limited.

It is possible that the slot extends continuously or intermittently at least partially around the circumference of the reinforcement means and/or that the slot is configured and/or shaped to allow a at least partially bending of the reinforcement means by allowing an at least partial compression of the slot.

There may be several slots aligned substantially along the longitudinal axis of the reinforcement means and also, additionally or alternatively, in radial direction around the circumference of the reinforcement means.

Additionally, it is possible that the slot is substantially parallel to the longitudinal axis of the reinforcement means, especially parallel to the longitudinal axis of the reinforcement means and/or that at least two slots are substantially parallel to each other and/or that at least two slots are substantially aligned along the same axis.

Moreover, it is possible that the reinforcement means comprises two or more interlocking annular elements, wherein at least one interlocking annular element is configured and/or shaped as to loosely interlock to at least one other interlocking element.

The interlocking annular elements may comprise e.g. a snap-fit design or the like. In particular, the snap-fit design may improve the capability of the interlocking annular elements to loosely interlock to at least one other interlocking element.

By the use of several, i.e. two or more interlocking annular elements, which form at least partially the reinforcement means, the advantage is achieved that the at least predetermined and/or customizable bending motion capabilities and the feature that the reinforcement means is configured such that the minimum bending radius of the lead is at least partially limited of the reinforcement means are improved, since the relative movement of the two or more interlocking annular elements may be predetermined by the design and shape of the two or more interlocking annular elements.

Furthermore, it is possible that the interlocking annular element is configured and/or shaped such that two interlocked and/or connected interlocking annular elements are forming the slot, wherein the slot is separating the two interlocked and/or connected interlocking annular elements and/or that at least two slots are provided, wherein especially at least two slots are provided between the two interlocked and/or connected interlocking annular elements.

Additionally, it is possible that the interlocking annular element comprises a plurality of teeth and a plurality of recesses.

Moreover, it is possible that one recess is provided between two teeth and/or that the teeth and recesses are provided at least one end of the interlocking annular elements, especially on both ends of the interlocking annular elements.

In particular, the teeth and recesses may be configured such that they form at least partially a snap-fit design or the like, wherein the snap-fit design is configured and/or shaped as to allow a loosely interlocking of interlocking elements.

Further, it is possible that the slot is formed between the teeth of a first teeth of a first interlocking annular element and a second teeth of a second interlocking annular element being connected to the first interlocking annular element.

Additionally, it is possible that the width and/or the wall size of the one or more slots substantially limits predetermined and/or customizable bending motion capabilities of the reinforcement means.

Furthermore, it is possible that the reinforcement means is at least partially made of metal, especially made of stainless steel and/or titanium or of a hard polymeric material, especially of PEEK and/or that the reinforcement means is at least partially encapsulated with a polymer, especially with an elastomer such as a silicone or a polyurethane, wherein the reinforcement means is especially partially or entirely encapsulated.

Moreover, the present invention relates to a lead with the features of claim 13. Accordingly, a lead is provided comprising at least one reinforcement means according to one of claims 1 to 12.

Especially, the lead may be a lead for neural applications, preferably a lead for a neurostimulation and/or neurorecording system. Such a neurostimulation and/or neurorecording system may be e.g. a DBS system.

The lead may e.g. comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or substantially the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

There may be an Active Lead Can element, which may comprise electronic means to address the plurality of electrodes and at least one Advanced Lead Can connecting means. Further, the Advanced Lead Can element may be hermetically or substantially hermetically sealed and may comprise electronic means to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 64 electrodes or more. The electrodes may be arranged such that the electrodes are substantially evenly distributed arranged all over the distal end of the lead.

Additionally, the present invention relates to a neurostimulation and/or neurorecording system according to claim 14. Accordingly, a neurostimulation and/or neurorecording system is provided, especially a deep brain stimulation (DBS) system, comprising at least one reinforcement means according to one of claims 1 to 12 and/or comprising at least one lead according to claim 13.

Furthermore, the present invention relates to an interlocking annular element for a reinforcement means for a lead according to claim 15. Accordingly, an interlocking annular element for a reinforcement means for a lead according to one of claims 1 to 12 is provided, comprising the interlocking annular element features, especially the characterizing features according to one of claims 6 to 11.

Figure 2:
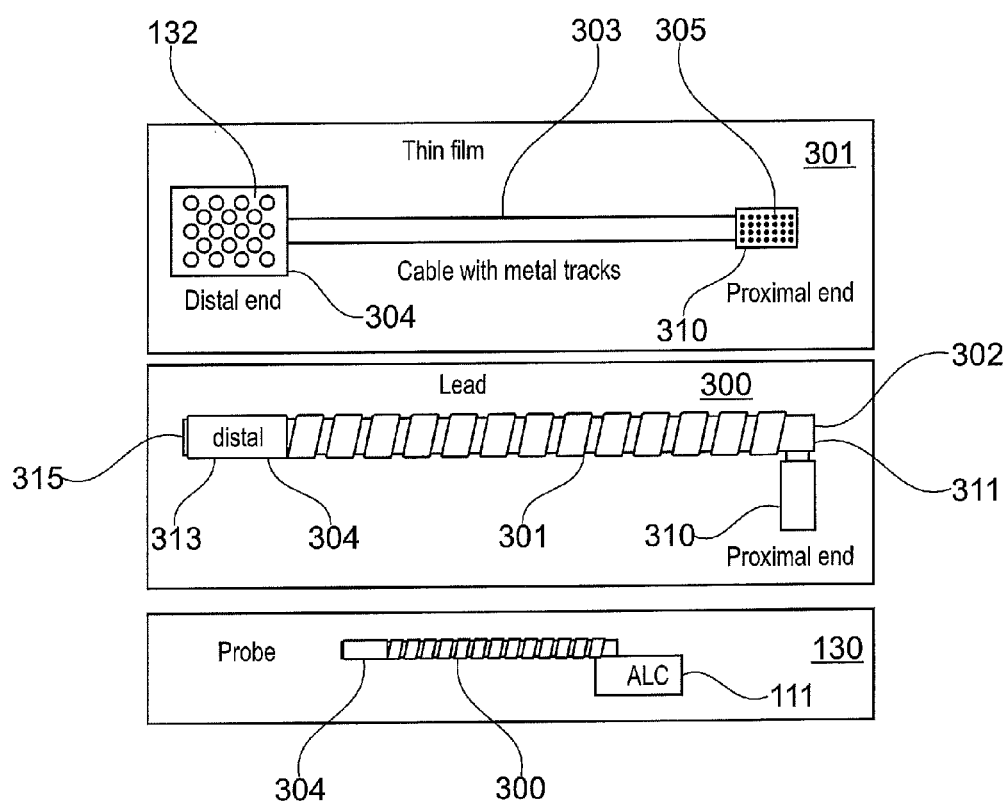
Figure 3:
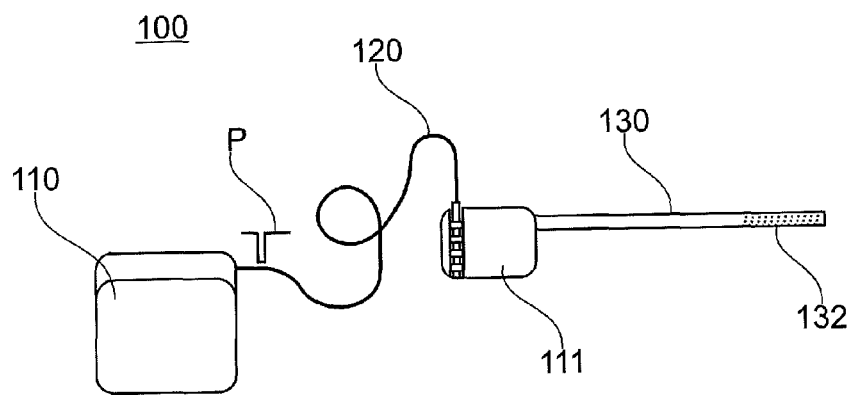
Figure 4:
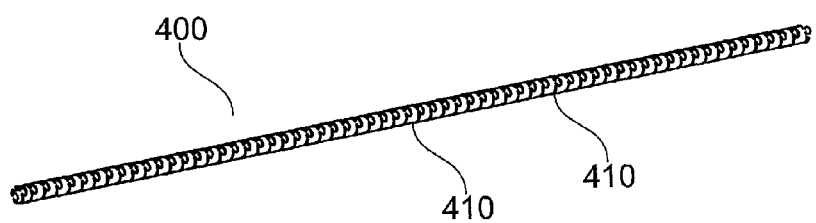
Figure 5:
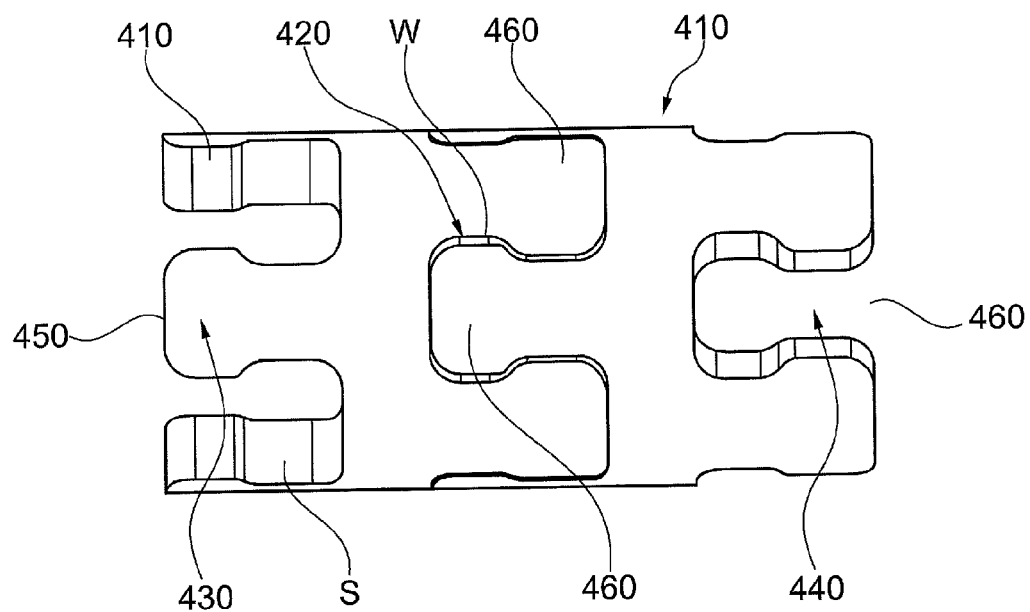
Figure 6:
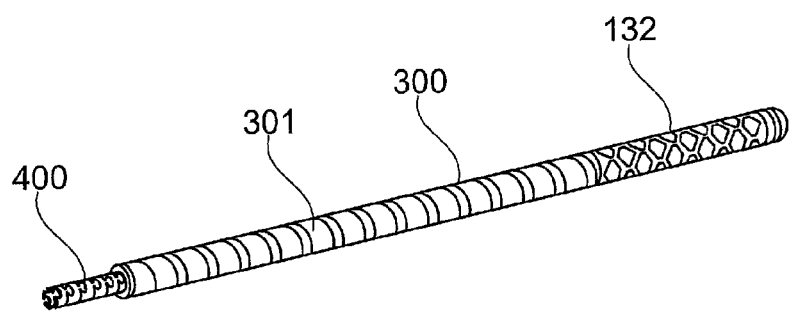

Further details and advantages of the present invention shall be described hereinafter with respect to the drawings:

FIG. 1 a schematical drawing of a neurostimulation system for deep brain stimulation (DBS);

FIG. 2 a further schematical drawing of a probe neurostimulation system for deep brain stimulation (DBS) and its components;

FIG. 3 a schematical drawing of a probe system according to the present invention;

FIG. 4 a schematical drawing of an embodiment of the reinforcement means having a tubular shape;

FIG. 5 a schematical drawing of the interlocking annular elements of the reinforcement means of FIG. 4; and FIG. 6 a schematical drawing of a lead comprising the reinforcement means of FIG. 4.

A possible embodiment of a neurostimulation system 100 for deep brain stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage or current pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

FIG. 2 further illustrates a typical architecture for a Deep Brain Stimulation probe 130 that comprises a DBS lead 300 and an Advanced Lead Can element 111 comprising electronic means to address electrodes 132 on the distal end 304 of the thin film 301, which is arranged at the distal end 313 and next to the distal tip 315 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the Advanced Lead Can element 111. The Advanced Lead Can element 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby e.g. 64 electrodes 132 can be provided on outer body surface at the distal end of the probe 130. By means of the extension wire 120 pulses P supplied by controller 110 can be transmitted to the Advanced Lead Can 111. The controller 110 can be an implantable pulse generator (IPG) 110.

FIG. 4 shows schematical drawing of an embodiment of the reinforcement means 400 having a tubular shape.

The reinforcement means 400 is a reinforcement means for a lead 300, especially a lead 300 for neural applications, preferably a lead 300 for a neurostimulation and/or neurorecording system 100 as shown in FIGS. 1 to 3.

The reinforcements means 400 has at least predetermined and/or customizable bending motion capabilities and is configured such that the minimum bending radius of the lead 300 is at least partially limited.

By this, the object is solved that medical leads with micro-fabricated electrode array and conductors require considerable care in handling due to the inherent fragility of the micro fabricated electrodes and/or conductors. In particular, the lead should not be subjected to uncontrolled bending because excessive bending can generate large mechanical stresses on the electrodes or conductors, which can lead to premature failure of the lead. The present invention provides a lead 300 with limited bending motion capabilities by means of the reinforcement means 400 allowing the lead to be functionally flexible enough (for instance to be bent in the burr-hole for a DBS lead) while preventing the lead to achieve radii of curvature that would damage the electrodes, traces or tracks of the implant.

The minimum bending radius achievable in a medical lead 300 is limited according to the invention by having a e.g. tube, i.e. the tubular reinforcement means 400 with predetermined and customizable bending motion capabilities.

The tubular reinforcement means 400 may be placed either inside the lead, over the lead or inside the insulation layer of the lead body.

Such a tubular reinforcement means 400 is similar to a flex shaft and is formed with several interlocking annular elements 410 shaped as to loosely interlock together as shown in FIG. 4.

As shown in FIG. 5, each interlocking annular element 410 is separated by a slot 420 which extends intermittently around the circumference of the annular element 420. The slots 420 are obtained using computer controlled techniques such as laser cutting, water jet cutting or other means and follow a path along the annular element 410 forming a plurality of teeth 430 and recesses 440 on opposite sides of the slot 420.

The interlocking annular element 410 comprises a plurality of teeth 430 and a plurality of recesses 440.

One recess 440 is provided between two teeth 430 and the teeth 430 and recesses 440 are provided at both ends 450, 460 of the interlocking annular elements 410.

The slot 420 is formed between the teeth 430 of a first tooth 430 of a first interlocking annular element 410 and a second tooth 430 of a second interlocking annular element 410 being connected to the first interlocking annular element 410.

The width W and/or the wall size S and/or the slot angle of the one or more slots 420 substantially limits predetermined and/or customizable bending motion capabilities of the reinforcement means 400. The gap or slot 420 between two adjacent annular elements 410 creates a loose joint allowing limited movement in any direction between the teeth 430 and the recesses 440, hence providing limited flexibility in all directions upon application of bending forces as well as tensile, compressive and torsion forces.

Such flexible tube 400, i.e. the tubular reinforcement means 400, can have different degrees of flexibility along its length by having the width W and/or the wall size S of the slot 420 varying along the length of the tube 400. The rigidity of the flexible tube 400 can also be varied through variations in design of the slot pattern.

To facilitate manufacturing and/or lead assembly, to provide protection to the reinforcement means 400 and for other reasons, the entire tube 400 may be encapsulated with an elastomer such a silicone or polyurethane, partially or entirely along the length of the tube.

The reinforcement means 400 is preferably made of metal such as stainless steel, titanium etc. or hard polymeric material such as PEEK.

The flexible reinforcement means 400, when placed in or over the lead body structures, provides a high level of flexibility over a predetermined range of bending radii dependent on the design of the slot pattern, the width of the slot as well as the tube material and the tube wall size. When the bending radius exceeds the predetermined bending range, the flexible flexible reinforcement means 400 becomes stiff preventing the lead 300 from bending further unless excessive bending load is applied.

The present invention can be applied for any medical lead where excessive bending of the device can lead to premature failure while lead functionality requires specific radii of curvature to be achieved. For instance DBS leads 300 as e.g. shown in FIGS. 3 and 6 are required to be bent at 90 degrees in the burr-hole with small radii of curvature.

While this is not an issue for traditional and existing DBS leads, future systems based on micro-fabricated thin film 301 conductors could be damaged if excessive bending is applied to the lead in the burr-hole or by the neurosurgeon during handling of the lead. The present invention provides a simple but effective solution to overcome this issue. For instance, a flexible reinforcement means 400 with predetermined bending range can be placed inside the silicone tube of the DBS lead 300, between its proximal end and distal end as shown in FIG. 3. The lead 300 is a lead having a thin film 301 with electrodes 132 at its distal end.

The invention claimed is:

1. A medical device system comprising:
    a medical lead including a carrier and a thin film, the thin film including a distal end, a proximal end, at least one electrode, and at least one electrically conductive track electrically coupled to the at least one electrode, wherein the at least one electrically conductive track extends from the at least one electrode towards the proximal end of the thin film, wherein the thin film is wound around the carrier, wherein the at least one electrode is configured to at least one of deliver electrical stimulation generated by an implantable medical device or sense electrical signals for delivery to the implantable medical device; and
    a reinforcement member configured to be positioned within the carrier such that the thin film is wound around the carrier and the reinforcement member, wherein the reinforcement member comprises a plurality of interlocking annular elements, wherein each interlocking annular element of the plurality of interlocking annular elements is loosely interlocked with another interlocking annular element such that the reinforcement member is bendable about a longitudinal axis of the reinforcement member.

2. The system of claim 1, wherein the reinforcement member has a tubular shape defined by the plurality of interlocking annular elements.

3. The system of claim 1, wherein the reinforcement member includes at least one slot formed between adjacent interlocking annular elements of the plurality of interlocking annular elements to allow the reinforcement member to be bendable about the longitudinal axis of the reinforcement member.

4. The system of claim 3, wherein the at least one slot comprises a plurality of slots arranged around a circumference of the reinforcement member.

5. The system of claim 4, wherein each slot of the plurality of slots is arranged substantially parallel to the longitudinal axis of the reinforcement member and the plurality of slots are substantially parallel to each other.

6. The system of claim 3, wherein each of the interlocking annular elements comprises a plurality of teeth and a plurality of recesses formed between respective teeth, wherein the at least one slot is formed between a first tooth of a first interlocking annular element and a second tooth of a second interlocking annular element adjacent and loosely interlocked to the first interlocking annular element.

7. The system of claim 3, wherein at least one of a width or wall size of the at least one slot substantially limits the bending of the reinforcement member about the longitudinal axis.

8. The system of claim 1, wherein the plurality of interlocking annular elements are formed of at least one of a metal or polymeric material.

9. The system of claim 1, wherein the reinforcement member is encapsulated by a polymeric material.

10. The system of claim 1, wherein each interlocking annular element comprises a plurality of teeth and a plurality of recesses formed between respective teeth, wherein respective teeth of a first interlocking annular element are located within respective recesses of a second interlocking annular element adjacent the first interlocking annular element to loosely interlock the first interlocking annular element to the second interlocking annular element.

11. The system of claim 1, wherein each interlocking annular element of the plurality of interlocking annular elements is loosely interlocked with another interlocking annular element to define a maximum bend of the reinforcement member about the longitudinal axis of the reinforcement member.

12. The system of claim 1, further comprising the implantable medical device, wherein the implantable medical device is configured to be electrically coupled to the at least one electrode of the thin film via the at least one electrically conductive track.

13. The system of claim 1, wherein the reinforcement member is configured to limit the bending of the medical lead about a longitudinal axis of the lead to a maximum radius of curvature when positioned within the carrier such that the thin film is wound around the carrier and the reinforcement member.

14. The medical device system of claim 1, wherein the carrier comprises silicone.

15. A method comprising inserting a medical lead system in tissue of a patient, wherein the medical lead system includes:
    a medical lead including a carrier and a thin film, the thin film including a distal end, a proximal end, at least one electrode, and at least one electrically conductive track electrically coupled to the at least one electrode, wherein the at least one electrically conductive track extends from the at least one electrode towards the proximal end of the thin film, and wherein the thin film is wound around the carrier, wherein the at least one electrode is configured to at least one of deliver electrical stimulation generated by an implantable medical device or sense electrical signals for delivery to the implantable medical device; and
    a reinforcement member configured to be positioned within the carrier such that the thin film is wound around the carrier and the reinforcement member, wherein the reinforcement member comprises a plurality of interlocking annular elements, wherein each interlocking annular element of the plurality of interlocking annular elements is loosely interlocked with another interlocking annular element such that the reinforcement member is bendable about a longitudinal axis of the reinforcement member.

16. The method of claim 15, further comprising placing the reinforcement member within the carrier of the medical lead prior to inserting the medical lead system in the tissue of the patient.

17. The method of claim 15, wherein inserting the medical lead system in the tissue of a patient comprises:
  inserting a distal portion of the medical lead system into the tissue of the patient via a burr hole in a skull of the patient when the reinforcement member is positioned within the carrier such that the thin film is wound around the carrier and the reinforcement member; and
  bending a portion of the medical lead system about a longitudinal axis of the medical lead while inserted within the burr hole, wherein the bending of the medical lead about the longitudinal axis is limited by the reinforcement member.

18. The method of claim 15, wherein the carrier comprises silicone.

19. A method comprising at least one of delivering electrical stimulation from an implantable medical device to a patient via at least one electrode of a medical lead system or sense electrical signals for delivery to the implantable medical device via the at least one electrode of the medical lead system, wherein the medical lead system includes:
  a medical lead including a carrier and a thin film, the thin film including a distal end, a proximal end, the at least one electrode, and at least one electrically conductive track electrically coupled to the at least one electrode, wherein the at least one electrically conductive track extends from the at least one electrode towards the proximal end of the thin film, wherein the thin film is wound around the carrier; and
  a reinforcement member configured to be positioned within the carrier such that the thin film is wound around the carrier and the reinforcement member, wherein the reinforcement member comprises a plurality of interlocking annular elements, wherein each interlocking annular element of the plurality of interlocking annular elements is loosely interlocked with another interlocking annular element such that the reinforcement member is bendable about a longitudinal axis of the reinforcement member.

20. The method of claim 19, wherein the carrier comprises silicone.

* * * * *